US00PP36382P2

(12) United States Plant Patent
Coggeshall et al.

(10) Patent No.: US PP36,382 P2
(45) Date of Patent: Jan. 14, 2025

(54) WALNUT TREE NAMED 'Hickman'

(50) Latin Name: ***Juglans nigra* cultivar**
Varietal Denomination: Hickman

(71) Applicant: THE CURATORS OF THE UNIVERSITY OF MISSOURI, Columbia, MO (US)

(72) Inventors: Mark V. Coggeshall, Columbia, MO (US); Ronald S. Revord, Columbia, MO (US); Nicholas A. Meier, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 18/416,651

(22) Filed: Jan. 18, 2024

(51) Int. Cl.
*A01H 5/10* (2018.01)
*A01H 6/00* (2018.01)

(52) U.S. Cl.
USPC ..... Plt./154

(58) Field of Classification Search
USPC ..... Plt./154
CPC ... A01H 5/10; A01H 5/08; A01H 5/04; A01H 5/00; A01H 6/00
See application file for complete search history.

(56) References Cited

PUBLICATIONS

University of Missouri Extension, Flowering and Fruit Characteristics of Black Walnut: A Tool for Identifying and Selecting Cultivars, retrieved on May 23, 2024 at https://extension.missouri.edu/publications/xm1001/2#compare, 2022, 9 pages. (Year: 2022).*
Jablonski B. First Quantitative Trait Loci Detected for Bearing Habit and Nut Quality Traits in Eastern Black Walnut (*Juglans nigra L.*) (Doctoral dissertation, University of Missouri-Columbia).
Meier N, Coggeshall MV, Webber JB, Bunting E, Revord RS. Genetic variation among 54 eastern black walnut cultivars for phenological and morphological traits. Journal of the American Society for Horticultural Science. Sep. 1, 2022;147(5):281-9.
Reid W, Coggeshall MV, Hunt KL. Cultivar evaluation and development for black walnut orchards. United States Department Of Agriculture Forest Service General Technical Report Nc. Jul. 25, 2004;243:18.

* cited by examiner

*Primary Examiner* — June Hwu
(74) *Attorney, Agent, or Firm* — McKee, Voorhees & Sease, PLC

(57) ABSTRACT

A new distinct *Juglans* plant named 'Hickman' is characterized by high-yield, abundant spur-bearing, medium nut and kernel size, and high kernel percentage. Taken together, 'Hickman' produces a high yield of kernels. The cultivar's nuts have a low to moderate rate of defects, and its kernel has good flavor and color quality. 'Hickman' is protogynous, with pistillate bloom beginning mid-season and extending about two-weeks and staminate bloom occurring mid-to-late season.

8 Drawing Sheets

Latin name: *Juglans nigra* cultivar.
Varietal denomination: 'Hickman'.

GOVERNMENT SUPPORT

This invention was made with government support under Grant No. 58-6020-0-007 awarded by the Agricultural Research Service. The Government has certain rights in the invention.

LATIN NAME

Botanical/commercial classification: *Juglans nigra* L., new black walnut tree cultivar.

CULTIVAR DENOMINATION

The cultivar denomination of the claimed black walnut cultivar is 'Hickman'.

BACKGROUND OF INVENTION

Missouri is home to a regional walnut industry based upon the nuts and kernels from eastern black walnut. Unique to most horticultural industries, the Missouri walnut industry is supported by nuts harvested from wild trees. Wild trees provide over 20 million pounds of in-shell nuts to the market during masting years, creating a footing for the industry. However, there are drawbacks to harvesting from an undomesticated species, namely, consistency in kernel quality and production and quite low kernel percentage per nut (10-14%). Orchard cultivation of improved eastern black walnut would standardize crop quality and supply, stabilizing the Missouri walnut industry and enabling possible growth.

Curation of nut-producing eastern black walnut cultivars began in New Franklin, Missouri in 1996 and a repository of over 50 historical cultivars is maintained there. These cultivars were selected by growers and enthusiasts over the twentieth century primarily based on high kernel percentage compared to the wild type (Reid 1990). While few of these historical cultivars have all the requisite traits needed to stand up large-scale orchard cultivation (e.g., productivity, low nut defect rate), they are an invaluable resource of breeding parentage (Reid et al., 2004). Consequently, breeding of eastern black walnut for orchard nut production began in 2002, establishing its first generation of offspring that year. Priority objectives include combining spur bearing with consistent high kernel percentage, mass, and light color. Spur bearing is the tendency for pistillate/nut production to occur on short, compacted branches that are 4 to 12 inches in length along a primary branch. The habit is comparable to that observed in apples (Reid, 1997) and appears to be expressed along a spectrum in eastern black walnut (Jablonski, 2023), considerably enhancing early and mature yield potential, distributing fruiting to many additional sites (buds) through the canopy. Spur bearing is documented in several cultivars (Reid et al., 2004) and is essential for future release for commercial orchard cultivation. The tree of the present cultivar, 'Hickman', produces extensive, precocious spur branches that bear nuts with a high kernel percentage and moderate mass.

BRIEF SUMMARY OF THE INVENTION

The present invention relates to a new and distinct cultivar of walnut tree (*Juglans nigra* L.) designated as 'Hickman'—a walnut tree with extensive precocious spurs and high kernel percentage and yield. The present invention is the first distinct cultivar release of the species from a dedicated breeding program for the orchard production of kernels and is found to be exhibiting the following combination of characteristics:

a) A high degree nuts produced on spur-type branches;
b) High kernel percentage;
c) High kernel yield through combining A and B;
d) Precociousness;
e) Well-filled, medium-sized nuts with a light color and low-moderate defect rate; and
f) Protogynous habit, with pistillate bloom beginning mid-season.

The new *Juglans nigra* walnut tree of the present invention was created at New Franklin, Missouri, by a controlled pollination between 'Sparks 127' and 'Football' in 2002. The controlled pollination was made using 'Sparks 127' as the female parent, fixing pollen exclusion bags over pistillate flowers prior to the stigmas becoming receptive. Pollen from 'Football' was administered into the bag using a hypodermic needle. Parentage was confirmed using expressed sequence tags simple sequence repeat (EST-SSRs) DNA markers, comparing alleles of 'Hickman' to its 'Sparks 127' and 'Football'. 'Sparks 127' and 'Football' both exhibit a spur bearing (Reid et al., 2004). Long-term evaluations in New Franklin, Missouri, show that nuts of 'Sparks 127' have a moderate kernel mass (averaging 5.6 g across years) with 31% kernel, while 'Football' has a larger kernel, averaging 6.1 g across years and 26% of nut mass (Meier et al., 2022). 'Football' average budbreak in New Franklin, Missouri, is April 15$^{th}$, while 'Sparks 127' occurs about a week later. Nuts from 'Sparks 127' are harvested in the early season, while 'Football' is harvested two weeks later. Both cultivars have typical, moderately high alternate bear indices.

Six progeny from this cross were planted at a research farm (New Franklin, Missouri) along with 114 additional control pollinated seedlings from this generation, representing 33 crosses, in a new seedling evaluation block in the fall of 2003 (FIG. 1). Evaluation of the progeny began in Year 5 (2007) when the most precocious seedlings began to bear nuts. Data were collected annually on phenological characters, nut quality traits, and yield parameters (bearing habit, yield efficiency, alternate bearing index), per the International Plant Genetic Resources Institute's Descriptors on Walnut (IPGRI, 1994). Phenological characters include bud break date, first and peak female flower bloom, first and peak male bloom, and harvest date. Nut samples were collected annually to evaluate shell appearance, width, length, and weight and cracked to measure kernel mass, percentage, color, venation, rate of defects. Kernel defects pertain to those that are unfilled, shriveled, moldy or decay, discoloration, or have another off character. A single tree, originally named '02.1055' and now designated 'Hickman', was selected from among the breeding generation for its superior spur bearing and consistent kernel quality. Compared to both parents, 'Sparks 127' and 'Football' respectively, 'Hickman' demonstrates a 2.5-3x greater degree of spur bearing per observation over Years 5 to 9. The kernel of 'Hickman' is modestly smaller than that of 'Sparks 127', while the kernel percentage is comparable to 'Sparks 127'.

The new cultivar of the present invention has been asexually propagated by grafting on open-pollinated seedlings of 'Thomas' as rootstock in selection blocks at Horticulture and Agroforestry Research Farm in New Franklin, Missouri. The distinctive characteristics of the new cultivar, particularly its propensity for spur bearing, have been found to be stable and are transmitted to the new trees when asexually propagated.

Designation of 'Hickman' is after Thomas Hickman, who built a brick Georgian-style home on the research farm in New Franklin, Missouri in 1819. The home is one of the state's oldest intact brick homes, was the first documented brick home built east of the Mississippi River and was added to the National Register of Historic Places in 2006 and rehabilitated in 2009.

BRIEF DESCRIPTION OF THE TABLES

Table 1. The top ten progeny of the 2002 breeding generation base on cumulative nuts produced.

Table 2. Nut characters of 'Hickman' compared to its parent, 'Football', and other eastern black walnut cultivars—means and standard errors summarized for four years, 2017, 2020, 2021, 2022.

Tabe 3. Nut yield of 'Hickman' in 2021 and 2023 compared to its parent, 'Football', and other eastern black walnut cultivars—means and standard deviation from a randomized block design trial planted in New Franklin, Missouri, in 2011.

DETAILED BOTANICAL DESCRIPTION

Botanical classification: *Juglans nigra.*

*Female parent.*—'Sparks 127'.

*Male parent.*—'Football'.

The description is based on the original seedling progeny (ortet) and subsequently grafted trees (ramets) established in a complete randomized replicated trial in New Franklin, Missouri. Data were collected on the seedling progeny from 2007 to 2010 (age 5-9) and grafted trees in replicate in 2017 and 2020-2023 (age 6 and 10-13). Common color terms are to be accorded their ordinary dictionary significance. The Munsell Color Charts for Plant Tissue (GretagMacbeth LCC, 617 Little Britain Road, New Windsor, NY 12553) was used to identify color.

Figure 1:
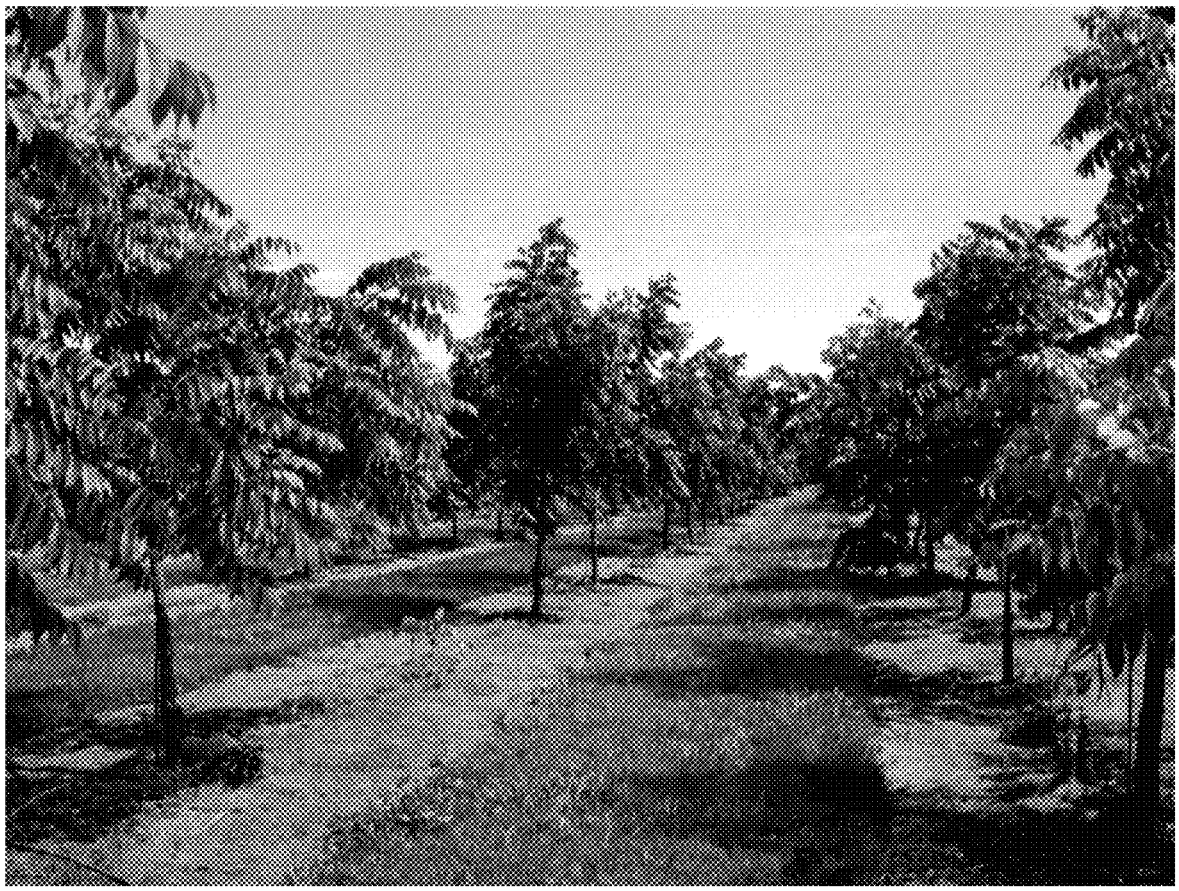
FIG. 1 shows the seedling block from which 'Hickman' was selected, taken on Jul. 17, 2008.
Figure 2:
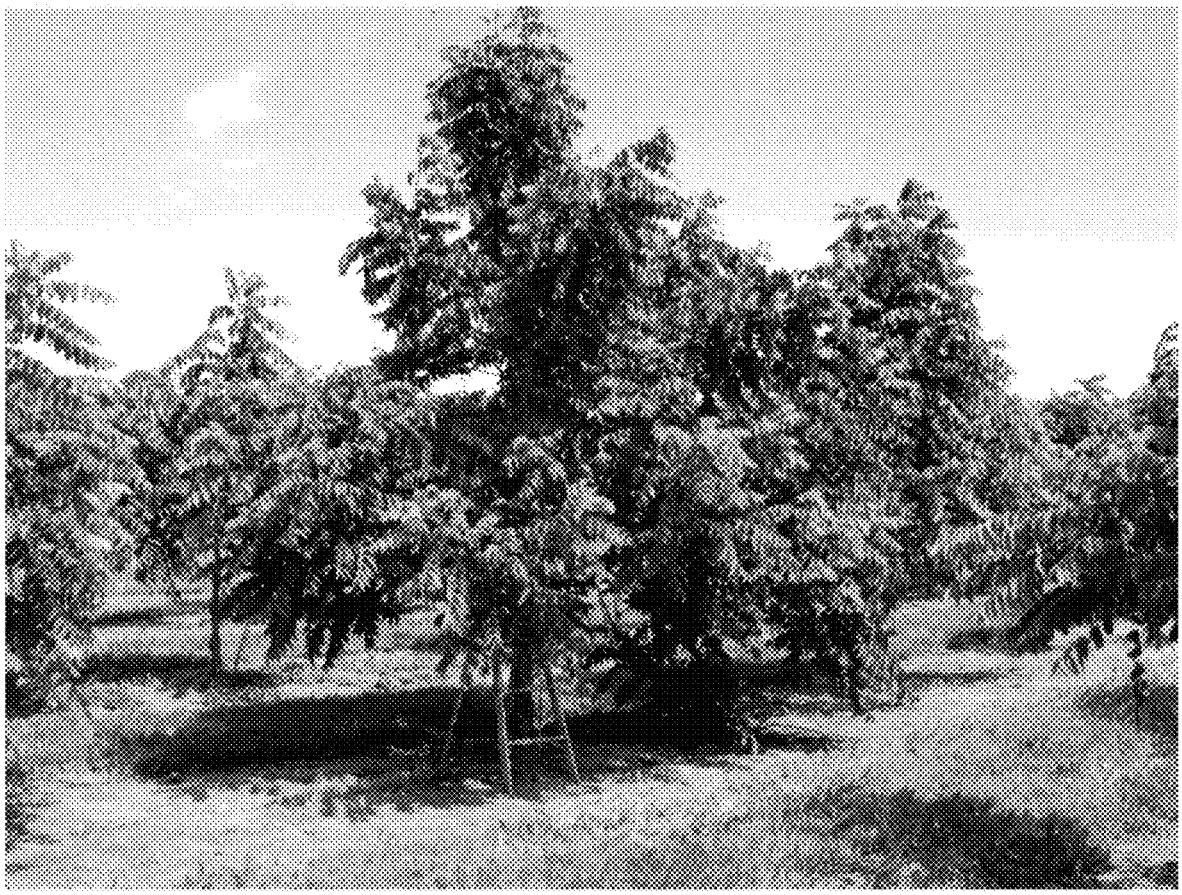
FIG. 2 shows the original seedling tree of 'Hickman' at age 6, taken on Jun. 17, 2008.
Figure 3:
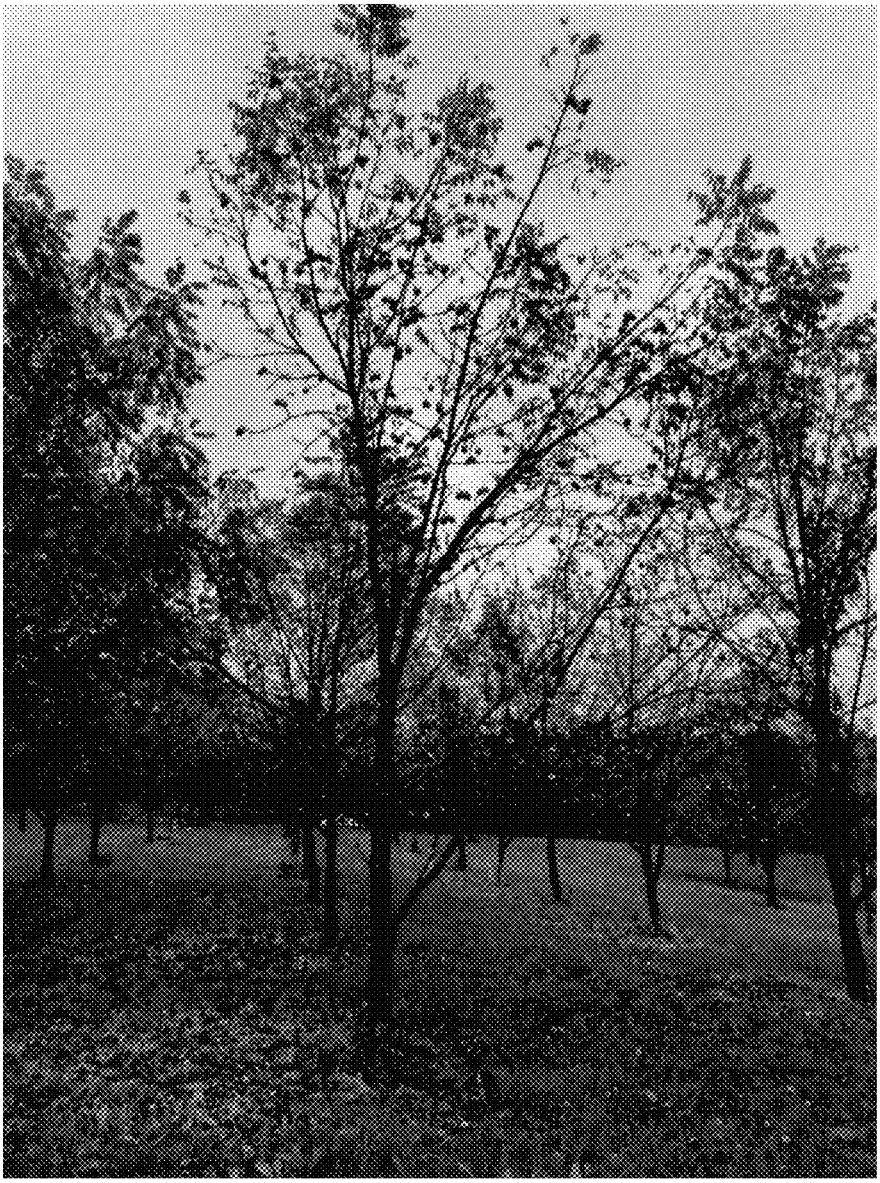
FIG. 3 shows a grafted 'Hickman' tree at age 9, with an upright, open branch growth habitat and abundant nuts borne on small, spur branches. The tree is defoliating before nuts have ripened for harvest.

Plant: The growth habit of the plant is illustrated in FIGS. 2 and 3. The ortet's trunk diameter 30 cm above the root collar was 16.8 cm and 18.3 cm in Years 8 and 9, respectively, and its height exceeded was approximately 4.5 m by age 7. Grafted trees (n=3) of 'Hickman' averaged a diameter 30 cm above the graft union of 9.0 cm at age 7, with an average height of 4.9 m and a canopy diameter of 3.58 meters. The tree is vigorous and semi-erect. The bark surface is deeply furrowed, ridged and is 5F 6/2 in color. Branch (7.5YR 4/2) habit displays upward growth with a forking, central leader shape. Lenticles are lighter in color (2.5Y 8/2), and about 2 mm in length and width. There are about 6 lenticles per $cm^2$. Terminal buds are flattened pyramidal, 2.5Y 6/4 in color, and are on average 9 mm in length.

Figure 4:
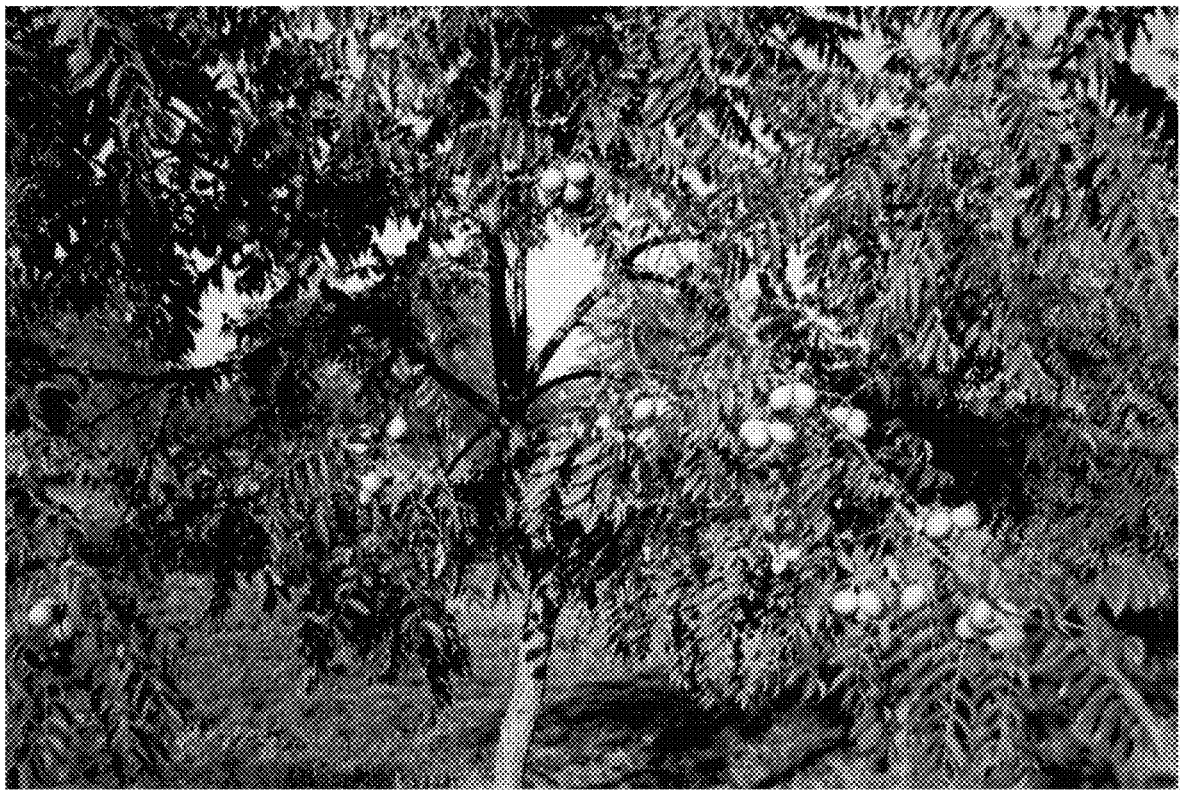
FIG. 4 shows spur bearing in clone of 'Hickman' grafted in 2015.
Figure 5:
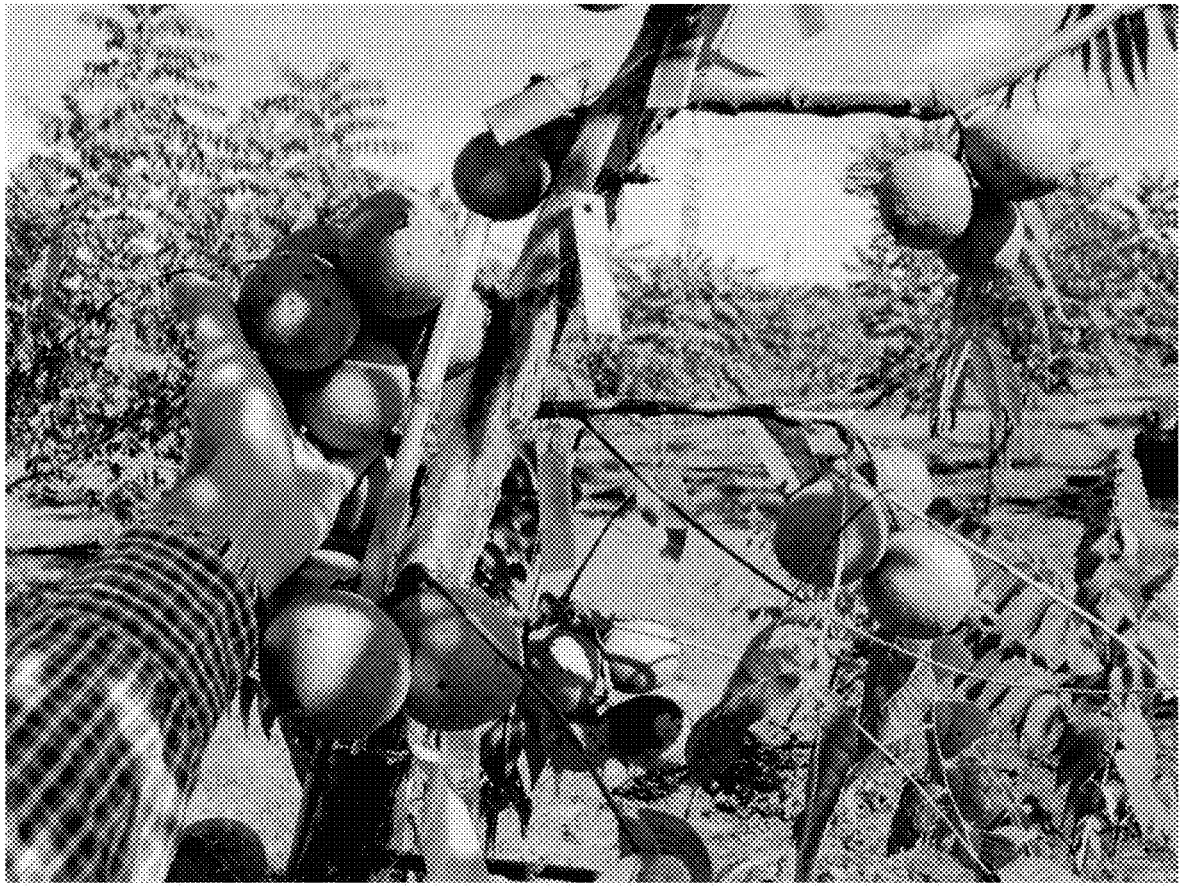
FIG. 5 displays nuts on spur branches of the central leader of the 'Hickman' ortert in its fifth growing season, 2007.

'Hickman' ortet display the earliest precocity observed within the breeding program, flowering in its fifth leaf, but importantly, it also displayed the greatest fecundity (TABLE 1). The seedling tree produced 656 nuts in its fifth leaf in 2007 and was the most productive offspring among the 120 seedlings in the 2002 breeding generation. By its eighth leaf in 2010, the ortet produced 1295 nuts and, despite a tendency to alternate bear, remained exceedingly the most productive offspring over this time period (TABLE 1). The next most productive progeny was 02.037.01 ('Brown Nugget x 'Daniel'), which produced 851 nuts by 2010. For context, only five of the other 118 other offspring produced over 600 nuts during this period. FIGS. 3, 4, and 5 displays the spur bearing habit of 'Hickman', where a great number of compact branches arise from larger limbs drastically increase the number of fruiting sites throughout the canopy. Short, compressed internodes terminating in pistillate blooms drives its prolific fecundity, and the habit is maintained across ramets (FIGS. 3 and 4).

Mature yield data was taken in replicated evaluations in 2021 and 2023 (Table 2). These data suggest 'Hickman' yields are comparable to the cultivars 'Sparrow' and 'Neel' and greater than the cultivar 'Football' as it reaches maturity, where 'Sparrow' is considered a yield standard (Reid et al 2004). Production in 2020 and 2022 was low due to alternate bearing, and observations suggest the alternate bearing tendency of 'Hickman' is comparable to its parents 'Sparks 127' and 'Football', which is reported by Reid et al (2004) as 0.84 and 1.00, respectively. However, alternate bearing of 'Hickman' is difficult to assess due to a gap in plot management from 2017 to 2019 resulting from to personnel turnover. While the performance of respective ramets vary within and between years, and ongoing evaluations are needed to fully depict 'Hickman' stability, 'Hickman' represents an improvement through combining early bearing (fifth leaf) and high fecundity with high mature yields.

Foliage: Bud break, where over 50% of terminal buds have enlarged and split to show green leaves, occurs mid to late season, on the $112^{th}$ day of the year (April $22^{th}$) on average. This date is comparable to 'Sparks 127' but after 'Football'. The leaves are typical of *Juglans nigra*, compound and leaflets alternate. Leaf length is 31 cm and width is 15 cm. Leaflets are narrow elliptical to elliptical in shape with a serrate margin. The middle leaflet averages 5 cm in width and 12 cm in length. Sixteen leaflets are on each leaf on average. Leaflet color is green (7.5GY 3/4) upper surface side and 5GY 6/6 in color on the lower surface. Rachis color is green yellow (2.5 GY 5/6) but turns to a yellowish later in the season. Leaflet margin is toothed, finely serrate. The upper leaf texture is smooth, slightly waxy, while the lower leaf texture is smooth. 'Hickman' tends to defoliate at or before harvest time, while rachises remain attached until later in the fall. Rachis average 21 cm in length. Petiole length is 7 mm and is 5Y 5/6 in color.

Figure 6:
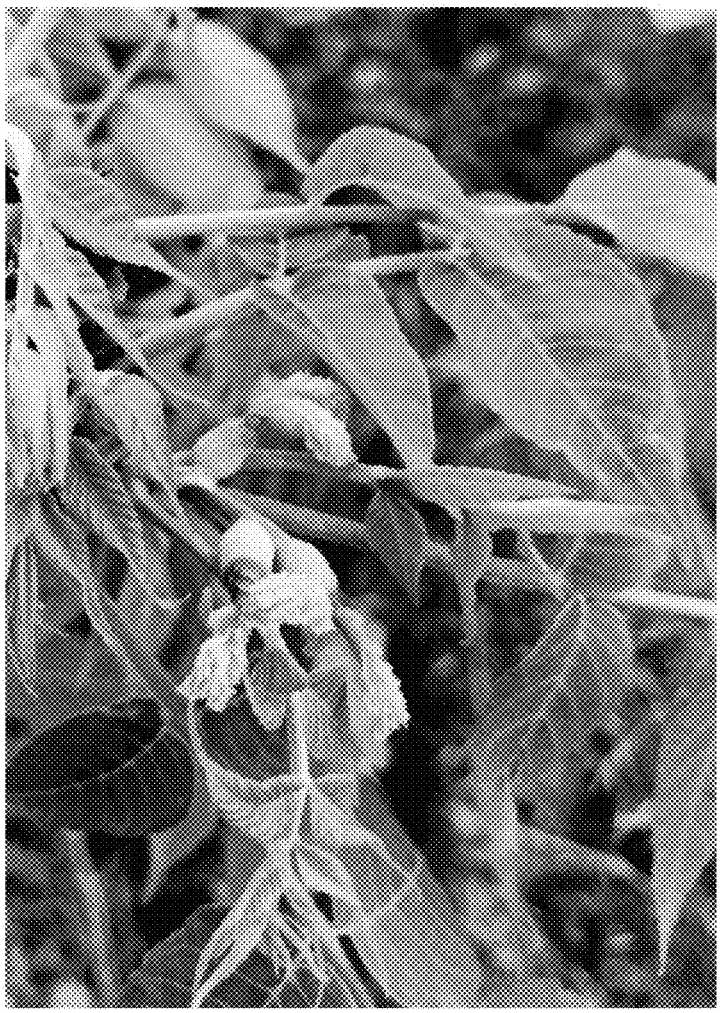
FIG. 6 show the pistillate flower of 'Hickman'.
Figure 7:
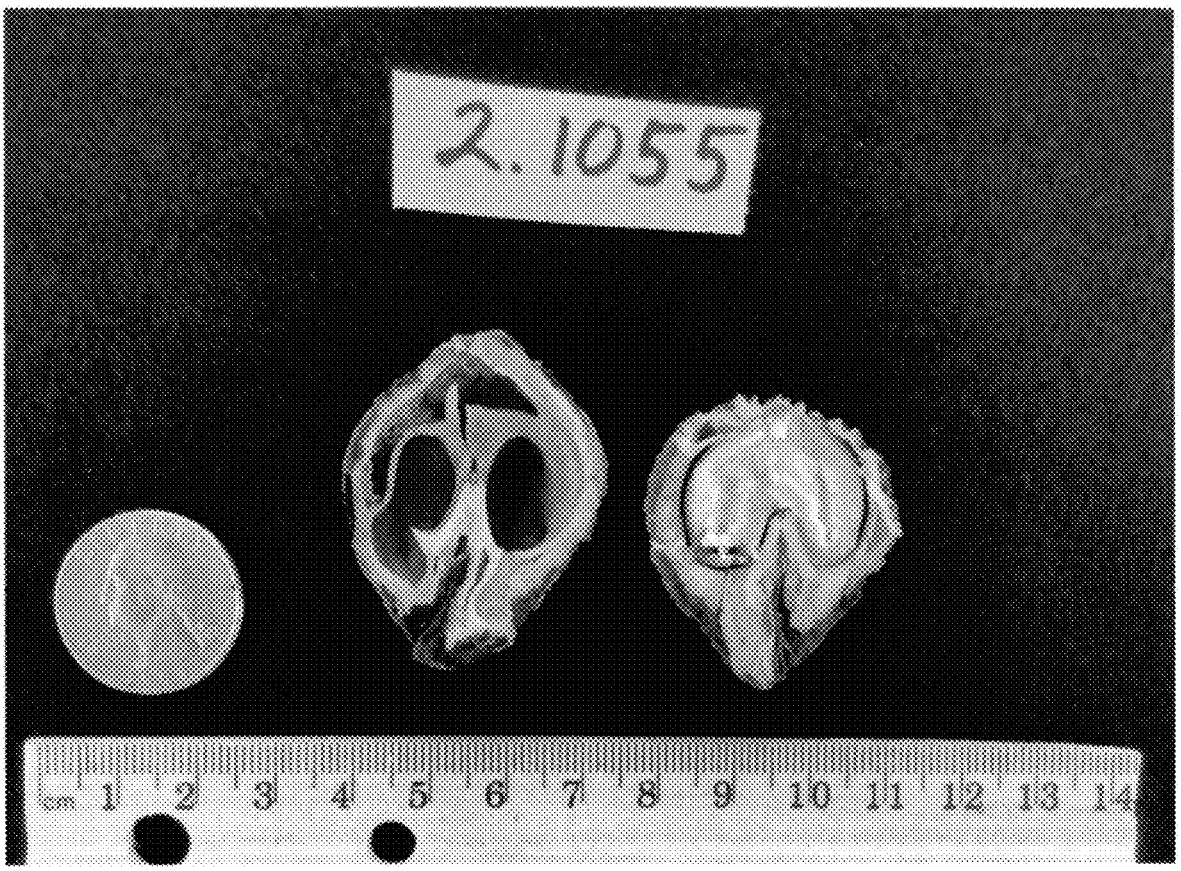
FIG. 7 shows a cross section of a 'Hickman' nut.

Inflorescence: The tree is precocious with its first flowers and nuts noted at age 5 years. Specifically, 83 pistillate flowers were recorded on the tree at age 5 years across 24 branches, from which 39 nuts developed. Male flowers (catkins) were also first present at age 5 years. 'Hickman' is protogynous. In replicated trials in 2017 and from 2020-2023, peak pistillate bloom occurred on the $124^{th}$ day of the year on average, and average male catkin bloom occurs on the $130^{th}$ day of the year. The female flowers are typical of *Juglans nigra* (FIG. 6), and the number of flowers per inflorescence range from 1-5. The flowers appear v-shaped as the two-stigmas extend during bloom, become receptive, and curve outward. Pistillate flowers are typically 8 to 10 mm at anthesis. There are no petals, and the female flowers are green (5GY 7/8) in color. The male flowers are borne on catkins, which range from 6 to 13 cm in length, and are green (5GY 7/8) in color before pollen shed.

Figure 8:
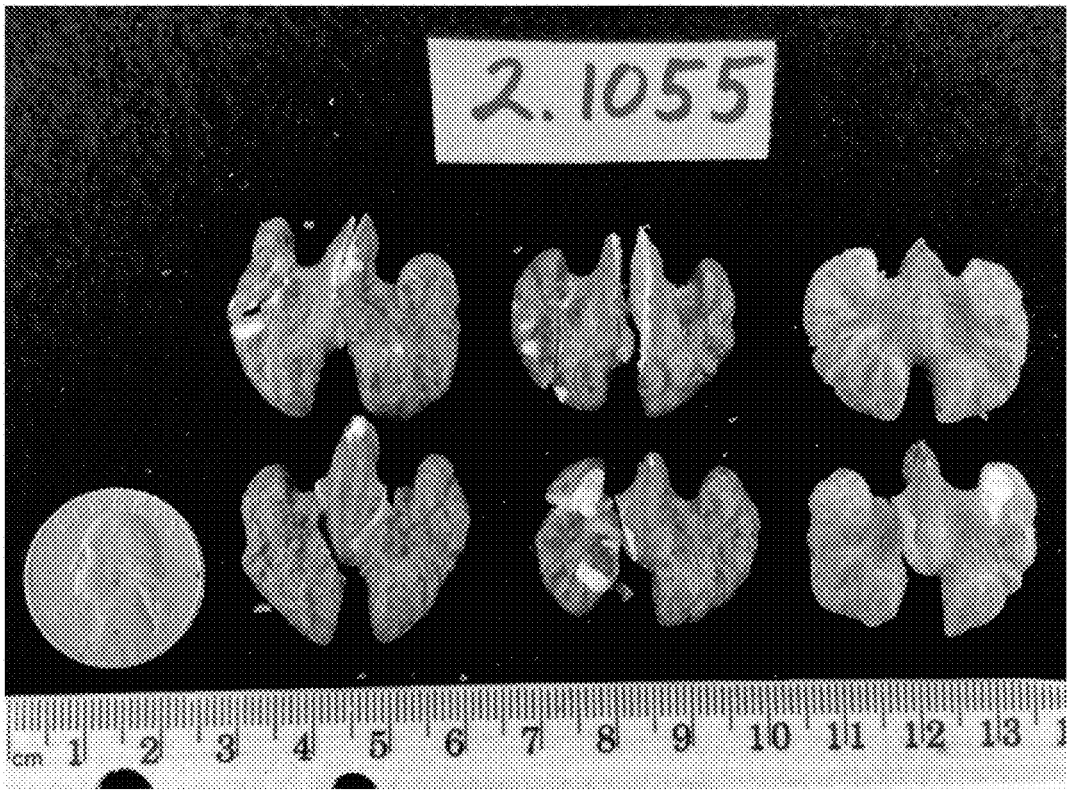
FIG. 8 shows kernel specimen of 'Hickman' from a grafted clone in replicated trial.

Walnuts: 'Hickman' is ripe for harvest on the $265^{th}$ day of the year on average in New Franklin, MO. The infructescence type is fascicled. The hull is small to medium in size (averaging 65 cm in length; 50 cm in diameter), non-dehiscent, and broad elliptic in shape. The hull thickness is 15 to 20 mm. The hull is green in color (2.5GY 6/8) but becomes yellowish green with ripening. The nut shape from a ventral view is broadly elliptic, although some appear broadly ovate, and is medium in size, averaging 16.0 g. Its cross section is oblate, and its base in ventral view is cuneate, while its apex is obtuse with a long nut tip. The extent of the pad around the suture is very weak limited to the upper extent of the nut. The shell is typical of *Juglans nigra*, grooved and thick. The shell's color is brown, 7.5YR 4/8. Average nut width face to face is 33.0 mm, and 29.1 mm suture to suture; length averages 39.1 mm. Shell thickness is 4-8 mm. With prompt hulling and cleaning, the kernel color is predominately light (7.5YR 9/4 to 7.5YR 7/8); however, delayed hulling stains kernels to a dark appearance (5YR 4/8) (FIG. 8, middle). Kernel weight averages 5.1 g and makes up 30.8% of the total nut weight. The nuts tend to fill well, and kernel percentage reaches 36% in years with ample rainfall in mid-Missouri—in these years the kernels are plump. Kernel venation is low, and the flavor is desirable. On average, over half of the kernel quarters are retrievable when cracking nuts individually. Nut defect rate varies annually, from 0% to 15%.

Disease susceptibility: Field observations of 'Hickman' suggest low tolerance to anthracnose, which likely contributes to its tendency to alternate bear.

Usage: This new cultivar of the present invention provides an eastern black walnut tree that has extensive precocious spur branches with high kernel percentage and yield, making it well-suited for the orchard production of nuts and kernels.

COMPARISONS WITH PARENT AND OTHER BLACK WALNUT CULTIVAR

TABLE 1

The top ten progeny of the 2002 breeding generation base on cumulative nuts produced.

| Progeny | Female Parent | Male Parent | Cumulative Nuts Produced 2007-2009 | Cumulative Nuts Produced 2007-2010 |
|---|---|---|---|---|
| Hickman | Sparks 127 | Football | 651 | 1295 |
| 02.037.01 | Br. Nugget | Daniel | 148 | 851 |
| 02.293.01 | Sparks 127 | Sparrow | 286 | 810 |
| 02.042.01 | Br. Nugget | Daniel | 215 | 796 |
| 02.248.03 | Sparks 127 | Emma K | 233 | 668 |
| 02.309.01 | Sparks 127 | Br. Nugget | 228 | 667 |
| 02.463.01 | Daniel | Emma K | 136 | 612 |
| 02.215.01 | Sauber #1 | Tomboy | 69 | 585 |
| 02.492.04 | Thomas/Myer | Br. Nugget | 191 | 569 |
| 02.216.02 | Sauber #1 | Emma K | 99 | 561 |

TABLE 2

Nut characters of 'Hickman' compared to its parent, 'Football', and other eastern black walnut cultivars - means and standard errors summarized for four years, 2017, 2020, 2021, 2022.

| Cultivar | Nut mass | Kernel mass | Kernel percentage |
|---|---|---|---|
| Hickman | 16.0 ± 0.29 | 5.1 ± 0.15 | 30.8 ± 0.26 |
| Football | 17.4 ± 0.14 | 5.0 ± 0.14 | 28.7 ± 0.25 |
| Neel | 19.1 ± 0.23 | 5.4 ± 0.09 | 28.5 ± 0.25 |
| Sparrow | 13.5 ± 0.21 | 4.7 ± 0.18 | 34.5 ± 0.36 |
| Sparks 147 | 15.7 ± 0.30 | 4.4 ± 0.18 | 29.4 ± 0.35 |

TABLE 3

Nut yield of 'Hickman' in 2021 and 2023 compared to its parent, 'Football', and other eastern black walnut cultivars - means and standard deviation from a randomized block design trial planted in New Franklin, Missouri, in 2011.

| Cultivar | Yield 2021 | Yield 2023 |
|---|---|---|
| Hickman | 29.6 ± 6.7 | 24.8 ± 8.5 |
| Football | 7.0 ± 2.2 | 12.6 ± 1.5 |
| Neel | 18.9 ± 4.5 | 24.8 ± 1.7 |
| Sparrow | 26.2 ± 4.7 | 23.8 ± 4.8 |

REFERENCES

International Plant Genetic Resources Institute (IPGRI). 1994. Descriptors for walnut (*Juglans* spp.). International Plant Genetic Resources Institute 54 p.

Jablonski, B. 2022. First quantitative trait loci detected for bearing habit and nut quality traits in eastern black walnut (*Juglans nigra* L.). (Doctoral dissertation, University of Missouri—Columbia).

Reid, W. 1990. Eastern black walnut: potential for commercial nut producing cultivars. In Advances in new crops. Proceedings of the first national symposium 'New crops: research, development, economics', Indianapolis, Indiana, USA, 23-26 Oct. 1988. (pp. 327-331). Timber Press.

Reid, W. 1997. Evaluation and management of black walnut for nut production. In Knowledge for the Future of Black Walnut: Proceedings of the Fifth Black Walnut Symposium: Held at Hammons Conference Center, Springfield, Missouri and Sho-Neff Plantation, Stockton, Missouri: Jul. 28-31, 1996 (Vol. 191, p. 211). North Central Forest Experiment Station, USDA Forest Service.

Reid, W., Coggeshall, M. V. and Hunt, K. L. 2004. Cultivar evaluation and development for black walnut orchards. United States Department of Agriculture Forest Service General Technical Report Nc, 243, p. 18.

Meier, N., Coggeshall, M. V., Webber, J. B., Bunting, E. and Revord, R. S. 2022. Genetic variation among 54 eastern black walnut cultivars for phenological and morphological traits. Journal of the American Society for Horticultural Science, 147(5), pp.281-289.

What is claimed is:

1. A new and distinct cultivar of black walnut tree designated 'Hickman' as shown and described herein.

* * * * *